(12) United States Patent
Jantz et al.

(10) Patent No.: US 8,338,157 B2
(45) Date of Patent: Dec. 25, 2012

US008338157B2

(54) RATIONALLY-DESIGNED MEGANUCLEASE VARIANTS OF LIG-34 AND I-CREI FOR MAIZE GENOME ENGINEERING

(75) Inventors: Derek Jantz, Durham, NC (US); James Jefferson Smith, Durham, NC (US)

(73) Assignee: Precision Biosciences, Inc., Durham, NC (US)

( * ) Notice: Subject to any disclaimer, the term of this patent is extended or adjusted under 35 U.S.C. 154(b) by 0 days.

(21) Appl. No.: 12/879,428

(22) Filed: Sep. 10, 2010

(65) Prior Publication Data

US 2011/0113509 A1    May 12, 2011

Related U.S. Application Data

(63) Continuation of application No. PCT/US2009/035719, filed on Mar. 2, 2009.

(60) Provisional application No. 61/035,613, filed on Mar. 11, 2008.

(51) Int. Cl.
 *C12N 9/22* (2006.01)
 *C07K 14/00* (2006.01)
(52) U.S. Cl. ........................................ 435/199; 530/350
(58) Field of Classification Search ............. 435/6, 69.1, 435/199, 320.1, 325, 23.2; 800/278
 See application file for complete search history.

(56) References Cited

U.S. PATENT DOCUMENTS

| | | | |
|---|---|---|---|
| 5,436,150 A | 7/1995 | Chandrasegaran |
| 5,474,896 A | 12/1995 | Dujon et al. |
| 5,527,695 A | 6/1996 | Hodges et al. |
| 5,744,336 A | 4/1998 | Hodges et al. |
| 5,789,215 A | 8/1998 | Berns et al. |
| 5,792,632 A | 8/1998 | Dujon et al. |
| 5,792,640 A | 8/1998 | Chandrasegaran |
| 5,830,729 A | 11/1998 | Jaisser et al. |
| 5,866,361 A | 2/1999 | Dujon et al. |
| 5,910,415 A | 6/1999 | Hodges et al. |
| 5,948,678 A | 9/1999 | Dujon et al. |
| 5,962,327 A | 10/1999 | Dujon et al. |
| 6,110,736 A | 8/2000 | Hodges et al. |
| 6,114,600 A | 9/2000 | Ow et al. |
| 6,238,924 B1 | 5/2001 | Dujon et al. |
| 6,265,196 B1 | 7/2001 | Chandrasegaran |
| 6,395,959 B1 | 5/2002 | Dujon et al. |
| 6,410,329 B1 | 6/2002 | Hansen et al. |
| 6,528,313 B1 | 3/2003 | Le Mouellic et al. |
| 6,528,314 B1 | 3/2003 | Le Mouellic et al. |
| 6,566,579 B1 | 5/2003 | Jaisser et al. |
| 6,610,545 B2 | 8/2003 | Dujon et al. |
| 6,638,768 B1 | 10/2003 | Le Mouellic et al. |
| 6,746,870 B1 | 6/2004 | Ow et al. |
| 6,781,032 B1 | 8/2004 | Gruissem et al. |
| 6,794,136 B1 | 9/2004 | Eisenberg et al. |
| 6,822,137 B1 | 11/2004 | Dujon et al. |
| 6,833,252 B1 | 12/2004 | Dujon et al. |
| 7,060,499 B1 | 6/2006 | Saito et al. |
| 7,098,031 B2 | 8/2006 | Choulika et al. |
| 7,126,041 B1 | 10/2006 | Helmer et al. |
| 7,135,608 B1 | 11/2006 | O'Gorman et al. |
| 7,214,536 B2 | 5/2007 | Dujon et al. |
| 7,271,000 B2 | 9/2007 | Dujon et al. |
| 7,285,538 B2 | 10/2007 | Choulika et al. |
| 7,309,605 B1 | 12/2007 | Dujon et al. |
| 7,351,877 B2 | 4/2008 | Suttie et al. |
| 7,476,539 B2 | 1/2009 | Saito et al. |
| 7,566,814 B2 | 7/2009 | O'Gorman et al. |
| 7,598,365 B2 | 10/2009 | D'Halluin et al. |
| 7,608,761 B2 | 10/2009 | Baley et al. |
| 7,632,985 B2 | 12/2009 | Malven et al. |
| 7,736,886 B2 | 6/2010 | Puchta et al. |
| 7,897,372 B2 | 3/2011 | Duchateau et al. |
| 8,021,867 B2 | 9/2011 | Smith et al. |
| 2002/0107214 A1 | 8/2002 | Choulika et al. |
| 2002/0110898 A1 | 8/2002 | Choulika et al. |
| 2002/0123145 A1 | 9/2002 | Ow |
| 2003/0113887 A1 | 6/2003 | Dujon et al. |
| 2003/0175968 A1 | 9/2003 | Golic et al. |
| 2003/0182670 A1 | 9/2003 | Dujon et al. |
| 2003/0229039 A1 | 12/2003 | Choulika et al. |
| 2004/0002092 A1 | 1/2004 | Arnould et al. |
| 2004/0019002 A1 | 1/2004 | Choulika et al. |
| 2004/0068761 A1 | 4/2004 | Golic et al. |
| 2004/0171154 A1 | 9/2004 | Storici et al. |

(Continued)

FOREIGN PATENT DOCUMENTS

EP            0317509 A2    5/1989

(Continued)

OTHER PUBLICATIONS

Silva et al., From Monomeric to Homodimeric Endonucleases and Back: Engineering Novel Specificity of LAGLIDADG Enzymes, 2006 J. Mol. Biol. 361:744-754.*
Rosen et al., Homing endonuclease I-CreI derivatives with novel DNA target specificities, Nucleic Acid Research 34(17): 4791-4800.*
Guo et al., Protein Tolerance to random amino acid change, 2004, PNAS 101(25): 9205-9210.*
Lu et al. Cre recombinase [Cloning vector pTurbo-Cre]. (2002) GenBank Accession AAK11472; pp. 1-2.*
International Search Report for International Application No. PCT/US09/35719 mailed Sep. 16, 2009. 10 pages.
Kaplinsky et al. Utility and Distribution of Conserved Noncoding Sequences in the Grasses. PNAS. Apr. 2002. 99(9):6147-6151. 5 pages.
Kaplinsky et al. Zea Mays LIGULELESS1 (lg1) Gene, Complete Cds, GenBank Accession No. AF451895 May 2002. [Retrieved from the Internet Sep. 2, 2009:<URL:http://www.ncbi.nlm.nih.gov/nuccore/17940733>]: p. 2, nucleotides 1261-2272, 2260-2281, 2271-3270. 3 pages.

(Continued)

*Primary Examiner* — Cathy Kingdon Worley
(74) *Attorney, Agent, or Firm* — Wilmer Cutler Pickering Hale and Dorr LLP

(57) ABSTRACT

The invention relates to the field of molecular biology and recombinant nucleic acid technology. In particular, the invention relates to a rationally-designed, non-naturally-occurring meganuclease with altered DNA recognition sequence specificity which recognizes and cleaves a unique DNA site in the maize genome. Disclosed herein are meganucleases which are variants of the I-CreI and LIG-34meganucleases. The invention also relates to methods of producing engineered maize plants using such meganucleases.

3 Claims, 3 Drawing Sheets

U.S. PATENT DOCUMENTS

| | | | |
|---|---|---|---|
| 2004/0203153 A1 | 10/2004 | Le Mouellic et al. |
| 2004/0250301 A1 | 12/2004 | Mouellic et al. |
| 2005/0026157 A1 | 2/2005 | Baltimore et al. |
| 2005/0032223 A1 | 2/2005 | Dujon et al. |
| 2005/0064474 A1 | 3/2005 | Urnov et al. |
| 2005/0172365 A1 | 8/2005 | Puchta et al. |
| 2005/0208489 A1 | 9/2005 | Carroll et al. |
| 2006/0078552 A1 | 4/2006 | Arnould et al. |
| 2006/0153826 A1 | 7/2006 | Arnould et al. |
| 2006/0206949 A1 | 9/2006 | Arnould et al. |
| 2006/0253918 A1 | 11/2006 | Que |
| 2006/0282911 A1 | 12/2006 | Bull et al. |
| 2006/0282914 A1 | 12/2006 | D'Halluin et al. |
| 2006/0288444 A1 | 12/2006 | McCarroll et al. |
| 2008/0083042 A1 | 4/2008 | Butruille et al. |
| 2009/0031438 A1 | 1/2009 | Kennard et al. |
| 2009/0133152 A1* | 5/2009 | Lyznik et al. ............... 800/275 |
| 2009/0286320 A1 | 11/2009 | O'Gorman et al. |

FOREIGN PATENT DOCUMENTS

| | | | |
|---|---|---|---|
| EP | 0602899 | | 6/1994 |
| EP | 0682112 | A1 | 11/1995 |
| EP | 1476547 | | 11/2004 |
| EP | 1485475 | | 12/2004 |
| EP | 1689870 | | 8/2006 |
| WO | WO-96/14408 | | 5/1996 |
| WO | WO-9955851 | A2 | 11/1999 |
| WO | WO-0046386 | A3 | 8/2000 |
| WO | WO-0111058 | A1 | 2/2001 |
| WO | WO-0123545 | A1 | 4/2001 |
| WO | WO-03004659 | A2 | 1/2003 |
| WO | WO-03025183 | A2 | 3/2003 |
| WO | WO-03038104 | A1 | 5/2003 |
| WO | WO-03074700 | A2 | 9/2003 |
| WO | WO-03078619 | A1 | 9/2003 |
| WO | WO-2004015134 | A2 | 2/2004 |
| WO | WO-2004031346 | A2 | 4/2004 |
| WO | WO-2004/067736 | A2 | 8/2004 |
| WO | WO-2004067753 | A2 | 8/2004 |
| WO | WO-2005049842 | A2 | 6/2005 |
| WO | WO-2005105989 | A1 | 11/2005 |
| WO | WO-2006032426 | A2 | 3/2006 |
| WO | WO-2006074956 | A1 | 7/2006 |
| WO | WO-2006097784 | A1 | 9/2006 |
| WO | WO-2006097853 | A1 | 9/2006 |
| WO | WO-2006097854 | A1 | 9/2006 |
| WO | WO-2006105946 | A2 | 10/2006 |
| WO | WO-2007034262 | A1 | 3/2007 |
| WO | WO-2007047859 | A2 | 4/2007 |
| WO | WO-2007049095 | A1 | 5/2007 |
| WO | WO-2007049156 | A2 | 5/2007 |
| WO | WO-2007057781 | A3 | 5/2007 |
| WO | WO-2007060495 | A1 | 5/2007 |
| WO | WO-2007093836 | A1 | 8/2007 |
| WO | WO-2007093918 | A2 | 8/2007 |
| WO | WO-2008010009 | A1 | 1/2008 |
| WO | WO-2008010093 | A2 | 1/2008 |
| WO | WO-2008021207 | A2 | 2/2008 |
| WO | WO-2008037436 | A1 | 4/2008 |
| WO | WO-2008093152 | A1 | 8/2008 |
| WO | WO-2008102274 | A2 | 8/2008 |
| WO | WO-2008145731 | A1 | 12/2008 |
| WO | WO-2008148559 | A1 | 12/2008 |
| WO | WO-2008152523 | A1 | 12/2008 |
| WO | WO-2009006297 | A2 | 1/2009 |
| WO | WO-2009114321 | A2 | 9/2009 |

OTHER PUBLICATIONS

Aagaard et al, Profile of the DNA recognition site of the archaeal homing endonuclease I-Dmol, Nucleic Acids Res. 1997, vol. 25. No. 8:1523-1530.

Adler, David A. et al. "Bioinformatics." Encyclopedia of Life Sciences. John Wiley & Sons Ltd. No month listed—2001, pp. 1-8.

Aggarwal et al., Novel site-specific DNA endonucleases, Structural Biology, 1998, vol. 8; pp. 19-25.

Allen et al., The Mutagenic potential of a single DNA double-strand break in a mammalian chromosome is not influenced by transcription, www.sciencedirect.com, DNA repair 2 (2003), pp. 1147-1156.

Argast et al., I-Ppol and I-Crel homing site sequence degeneracy determined by random mutagenesis and sequential in vitro enrichment, J. Mol. Biol., 1998, pp. 345-353, vol. 280.

Arnould et al., Engineered I-Crel Derivatives Cleaving Sequences from the Human XPC Gene can Induce Highly Efficient Gene Correction in Mammalian Cells. J. Mol. Biol. 371, Elsevier Ltd. pp. 49-65. May 10, 2007.

Arnould et al., Engineering of large numbers of highly specific homing endonucleases that induce recombination of novel DNA targets, J. Mol. Biol., 2006, pp. 443-458, vol. 355.

Ashworth et al. Jun. 2006. Computational redesign of endonucleases DNA binding and cleavage specificity. Nature, 441, 656-659.

Belfort et al., Homing enconucleases: keeping the house in order, Nucleic Acids Research, 1997, vol. 25, No. 17, pp. 3379-3388.

Beumer et al., Efficient gene targeting in drosophila with zinc-finger nucleases, Genetics, Apr. 2006, 172, pp. 2391-2403.

Bibikova et al., Enhancing gene targeting with designed zinc finger nucleases, Science, May 2, 2003, p. 764, vol. 300.

Bibikova et al., Stimulation of homologous recombination through targeted cleavage by chimeric nucleases, Molecular and Cellular Biology, Jan. 2001, pp. 289-297, vol. 21 No. 1.

Bibikova et al., Targeted chromosomal cleavage and mutagenesis in drosophila using zinc-finger nucleases, Genetics, Jul. 2002, 161, pp. 1169-1175.

Bolduc et al. Revised Sep. 2003. Structural and biochemical analyses of DNA and RNA binding by a bifunctional homing endonuclease and group I intron splicing factor. Genes Dev, 17, 2875-2888.

Butaye et al., Approaches to Minimize Variation of Transgene Expression in Plants, Molecular Breeding, vol. 16 No. 1, Aug. 1, 2005, pp. 79-91, XP019258738.

Cahill et al. (2006), Mechanisms of eukaryotic DNA double strand break repair, *Front. Biosci.* 11:1958-1976.

Chames et al., In vivo selection of engineered homing endonucleases using double-strand break induced homologous recombination, Nucleic Acids Research, 2005, vol. 33, No. 20. 10 pages.

Chen et al., A highly sensitive selection method for directed evolution of homing endonucleases, Nucleic Acids Research, 2005, pp. 1-7, vol. 33 No. 18 e154.

Chen, R. Jan. 1, 2001. Enzyme engineering: rational redesign versus directed evolution. Trends Biotechnol, 19, 13-14.

Chevalier B. S. et al. "Homing Endonucleases: Structural and Functional Insight Into the Catalysts of Intron/Intein Mobility." Nucleic Acids Research. Oxford University Press. Surrey, Great Britain. vol. 29, No. 18, Apr. 30, 2001. pp. 3757-3774.

Chevalier et al., Design, activity, and structure of a highly specific artificial endonuclease, Molecular Cell, Oct. 2002; vol. 10: pp. 895-905.

Chevalier et al., Flexible DNA target site recognition by divergent homing endoculease isoschizomers I-Crel and I-Msol, J. Mol. Biol., 2003, pp. 253-269, vol. 329.

Chevalier et al., Metal-dependent DNA cleavage mechanism of the I-Crel LAGLIDADG homing endonuclease, Biochemistry, 2004, pp. 14015-14026, vol. 43.

Chevalier et al., The homing endonuclease I-Crel uses three metals, one of which is shared between the two active sites, Nature Structural Biology, Apr. 2001, pp. 312-316, vol. 8 No. 4.

Chilton et al., Targeted integration of T-DNA into the Tobacco Genome at double-stranded breaks: New insights on the mechanism of T-DNA integration, Plant Physiology, Nov. 2003, vol. 133, pp. 956-965.

Cozzone, Alain J. "Proteins: Fundamental Chemical Properties." Encyclopedia of Life Sciences. No month listed—2002. John Wiley & Sons Ltd. pp. 1-10.

D'Halluin et al., Homologous recombination: A basis for targeted genome optimization in crop species such as maize, Plaint Biotechnology Journal, Jan. 2008, vol. 6, No. 1, pp. 93-102, XP002501442.

Dalgaard, Jacob Z. et al. "A Site-Specific Endonuclease Encoded by a Typical Archaeal Intron." Proc. Natl. Acad. Sci. Jun. 1993. vol. 90. pp. 5414-5417.

Desjarlais et al., Use of a zinc-finger consensus sequence framework and specificity rules to design specific DNA binding proteins, Proc. Natl. Acad. Sci. USA, Mar. 1993, pp. 2256-2260, vol. 90.

Dhanasekaran et al., Designer zinc finger proteins: tools for creating artificial DNA-binding functional proteins, Acc. Chem. Res., 2006, pp. 45-52, vol. 39 No. 1.

Doyon et al., Directed evolution and substrate specificity profile of homing endonuclease I-SceI, J. Am. Chem. Soc., 2006, pp. 2477-2484, vol. 128.

Duan et al., Crystal structure of PI-SceI, a homing endonuclease with protein splicing activity. Cell, May 16, 1997, vol. 89, pp. 555-564.

Durai et al., Zinc finger nucleases: custom-designed molecular scissors for genome engineering of plant and mammalian cells. Nucleic Acids Res, Oct. 26, 2005, vol. 33; pp. 5978-5990.

Epinat, A Novel Engineered Meganuclease Induces Homologous Recombination in Yeast and Mammalian Cells, Nucleic Acids Research, 2003, vol. 31, No. 11, pp. 2952-2962.

European Office Action, European Patent Application No. 06 826 293.0, dated Nov. 20, 2008. 3 pages.

European Search Report for European Patent Application No. 10191885.2 mailed Apr. 26, 2011. 12 pages.

European Search Report for European Patent Application No. 10191888.6 mailed May 18, 2011. 5 pages.

European Search Report for European Patent Application No. 10191904.1 mailed May 13, 2011. 9 pages.

Fitzsimons Hall et al., Creation of an artificial bifunctional intein by grafting a homing endonuclease into a mini-intein, J. Mol. Biol., 2002, pp. 173-179, vol. 323.

Gimble et al., Assessing the plasticity of DNA target site recognition of the PI-SceI homing endonuclease using a bacterial two-hybrid selection system. J Mol Biol, Oct. 2003, vol. 334; pp. 993-1008.

Gimble, F.S. Engineering Homing Endonulceases for Genomic Applications. In Homing Endonucleases and Inteins. Belfort, Derbyshire, Stoddard and Woods, Eds. Springer-Verlag, Berlin Heidelberg. No month listed—2005. 16 pages.

Gogarten et al., Inteims: Structure, Function and Evolution, Annu. Rev. Microbiol., 2002, 56, pp. 263-287.

Gorbumova et al., Non-Homologous DNA end joining in Plant Cells is associated with deletions and filler DNA insertions, Nucleic Acids Research, 1997, vol. 25, No. 22.

Gouble et al. "Efficient in toto Targeted Recombination in Mouse Liver by Meganuclease-induced Double-strand Break." The Journal of Gene Medicine. Feb. 13, 2006. Wiley Interscience. vol. 8. p. 616-622.

Gremillon et al. (2004), New Plant growth-modifying properties of the Agrobacterium T-6b oncogene revealed by the use of a dexamethasone-inducible promoter, *Plant J.* 37:218-228.

Grindl et al., The protein splicing domain of the homing endonuclease PI-SceI is responsible for specific DNA binding, Nucleic Acids Research, 1998, vol. 26, No. 8, pp. 1857-1862.

Gruen et al., An in vivo selection system for homing endonuclease activity, Nucleic acids research, 2002, vol. 30, No. 7.

Guhan et al., Structural and functional characteristics of homing endonucleases, Critical Reviews in Biochemistry and Molecular Biology, 2003, pp. 199-248, vol. 38 No. 3.

Harris, J.L. and Craik, C.S. Engineering enzyme specificity. Curr Opin Chem Biol, No month listed—1998 vol. 2, pp. 127-132.

Heath, Patrick J. et al. "The Structure of I-CreI, A Group I Intron-encoded Homing Endonuclease." Nature Structural Biology. vol. 4, No. 6. Jun. 1997. pp. 468-476.

Hu et al. "Probing the Structure of the PI-SceI-DNA Complex by Affinity Cleavage and Affinity Photcross-linking." The Journal of Biological Chemistry. Jan. 28, 2000. vol. 275, No. 4. pp. 2705-2712.

Ichiyanagi et al., Crystal structure of an archaeal intein-encoded homing endonuclease PI-PfuI, J. Mol. Biol., 2000, pp. 889-901, vol. 300.

International Search Report from PCT/US2006/040919, mailed Aug. 29, 2007. 11 pages.

Jurica, et al., DNA recognication and cleavage by the LAGLIDADG homing endonuclease I-CreI, Molecular Cell, Oct. 1998, vol. 2: pp. 469-476.

Jurica, M.S. et al. "Homing Endonucleases: Structure, Function and Evolution." CMLS: Cellular and Molecular Life Sciences. Feb. 1999. vol. 55. pp. 1304-1326.

Liang et al. "Genetic Fusion of Subunits of a Dimeric Protein Substantially Enhances its Stability and Rate of Folding." Proc. Natl. Acad. Sci. vol. 90. Aug. 1993. pp. 7010-7014.

Lloyd et al., Targeted mutagenesis using zinc-finger nucleases in arabidopsis, PNAS, Feb 8, 2005, vol. 102, No. 6, pp. 2232-2237.

Looger, L. et al., Computational Design of Receptor and Sensor Proteins with Novel Functions, Nature, 2003, pp. 185-190, vol. 423 No. 6936.

Lorence and Verpoorte (2004), Gene Transfer and Expression in Plants, *Methods Mol. Biol.*, 267: 329-50.

Lucas et al., Rapid evolution of the DNA-binding site in LAGLIDAG homing endonucleases, Nucleic Acids Research, 2001, pp. 960-969, vol. 29 No. 4.

Maggert et al., Highly efficient sex chromosome interchanges produced by I-CreI expression in Drosophila, Genetics, Nov. 2005, pp. 1103-1114, vol. 171.

Mani et al., Binding of two zinc finger nuclease monomers to two specific sites is required for effective double-strand DNA cleavage, Biochemical and Biophysical Research Communications, Jul. 2005, pp. 1191-1197, vol. 334.

Mani et al., Design, engineering, and characterization of zinc finger nucleases, Biochemical and Biophysical Research Communications, Jun. 2005, pp. 447-457, vol. 335.

Manivasakam et al., Restriction enzymes increase efficiences of illegitimate DNA integration But decrease homologous integration in mammalian cells, Nucleic Acids Research, 2001, vol. 29, No. 23. 8 pages.

Matsumura et al. Feb. 21, 2006. Crystal structure of intein homing endonuclease II encoded in DNA polymerase gene from hyperthermophilic archaeon Thermococcus kodakaraensis strain KOD1. Proteins, vol. 63; pp. 711-715.

McDaniel et al., Advances in synthetic biology: on the path from prototypes to applications, Current Opinion in Biotechnology, 2005, pp. 476-483, vol. 16.

Miller et al., An improved zinc-finger nuclease architecture for highly specific genome editing, Nature Biotechnology, Jul. 2007, vol. 25, No. 7.

Monnat et al., Generation of highly site-specific DNA double-strand breaks in human cells by the homing endonucleases I-PpoI and I CreI, Biochemical and Biophysical Research Communications, 1999, pp. 88-93, vol. 255.

Moure et al., Crystal structure of the intein homing endonuclease PI-SceI Bound to its Recognition Sequences, Nature Structural Biology, Oct. 2002, vol. 9, No. 10, pp. 764-770.

Moure et al., The crystal structure of the gene targeting homing endonuclease I-SceI reveals the origins of its target site specificity. J Mol Biol, Sep. 2003, vol. 334, pp. 685-695.

Omirulleh et al. (1993), Activity of a chimeric promoter with the doubled CaMV 35S enhancer element in protoplast-derived cells and transgenic plants in maize, *Plant Molecular Biology*, 21:415-428.

Orel et al., Different Pathways of Homologous Recombination are used for the repair of double-strand breaks within tandemly arranged sequences in the plant genome, The Plant Journal, 2003, 35, pp. 604-612.

Pabo et al., Transcription factors: structural families and principles of DNA recognition, Annu. Rev. Biochem., 1992, pp. 1053-1095, vol. 61.

Pace, C. Nick et al. "Protein Stability." Encyclopedia of Life Sciences. No month listed—2001. John Wiley & Sons Ltd. pp. 1-4.

Pacher et al., Two unlinked couble-strand breaks can induce reciprocal exchanges in plant genomes via homologous recombination and nonhomologous end joining, Genetics, 2007. 9 pages.

Perler, InBase, The Intein Database, Nucleic Acids Research, 2000, vol. 28, No. 1. 2 pages.

Poland, Bradley W. et al. "Structural Insights into the Protein Splicing Mechanism of PI-SceI." The Journal of Biological Chemistry. Jun. 2000. vol. 275, No. 22. pp. 16408-16413.

Porteus et al., Gene Targeting Using Zinc Finger Nucleases, Nature Biotechnology, Aug. 2005, vol. 23., No. 8, pp. 967-973.

Porteus, Mammalian gene targeting with designed zinc finger nucleases, Molecular Therapy, Feb. 2006, pp. 438-446, vol. 13 No. 2.

Prieto et al., "The C-terminal loop of the homing endonuclease I-CreI is essential for site recognition, DNA binding and cleavage, "Nucleic Acids Research vol. 35 No. 10; pp. 3262-3271, 2007.

Puchta et al., Homologous Recombination in Plant Cells is Enhanced By In Vivo Induction of Double Strand Breaks into DNA by a Site-Specific Endonuclease, Nucleic Acids Research, 1993, vol. 21, No. 22. 7 pages.

Puchta et al., Two different but related mechanisms are used in plants for the repair of genomic double-strand breaks by homologous recombination, Proc. Natl. Acad. Sci. USA, May 1996, pp. 5055-5060, vol. 93.

Puchta, The Repair of Double-Strand Breaks in Plants; Mechanisms and Consequences for Genome Evolution, Journal of Experimental Botany, Jan. 2005, vol. 56, No. 409, pp. 1-14.

Rong et al., Gene Targeting by homologous recombination in drosophila, www.sciencemag.org, Jun. 2000, vol. 288. 7 pages.

Rong et al., Targeted mutagenesis by homologous recombination in D. Melanogaster, downloaded from www.genesdev.org on Feb. 25, 2011. 15 pages.

Rosen et al. Sep. 13, 2006. Homing endonuclease I-CreI derivatives with novel DNA target specificities. Nucleic Acids Res, vol. 34., No. 17; pp. 4791-4800.

Rouet et al., Introduction of double-strand breaks into the genome of mouse cells by expression of a rare-cutting endonuclease, Molecular and Cellular Biology, Dec. 1994, pp. 8096-8106, vol. 14 No. 12.

Sali et al. "Comparative Protein Modelling by Satisfaction of Spatial Restraints." J. Mol. Biol. Jul. 1993. pp. 779-815.

Salomon, et al. (1998), Capture of genomic and T-DNA sequences during double-strand break repair in somatic plant cells, *EMBO J.* vol. 17, No. 20, pp. 6086-6095.

Seligman et al., Genetic Analysis of the Chlamydomonas reinhardtii I-CreI mobile intron homing system in *Escherichia coli*, Genetics, Dec. 1997, pp. 1653-1664, vol. 147.

Seligman et al., Mutations altering the cleavage specificity of a homing endonuclease, Nucleic Acids Research, 2002, vol. 30, No. 17, pp. 3870-3879.

Shen et al. DNA binding and cleavage by the HNH homing endonuclease I-HmuI. J Mol Biol, Jul. 2004, vol. 342, pp. 43-56.

Siebert et al., Efficient repair of genomic double-strand breaks by homologous recomination between directly repeated sequences in the plant genome, The Plant Cell, May 2002, vol. 14, pp. 1121-1131.

Silva et al., Analysis of the LLAGLIDADG interface of the monomeric homing endonuclease I-Dmol, Nucleic Acids Research, 2004, vol. 32, No. 10, pp. 3156-3168.

Silva et al., Crystal structure of the thermostable archaeal intron-encoded endonuclease I-Dmol, J. Mol. Biol., 1999, pp. 1123-1136, vol. 286.

Silva, George H. et al. "From Monomeric to Homodimeric Endonucleases and Back: Engineering Novel Specificity of LAGLIDADG Enzymes." J. Mol. Biol. Jul. 2006. pp. 744-754.

Singh et al. (2003), Isolation and characterization of a flowering plant male gametic cell-specific promoter, FEBS Lett. 542:47-52.

Smith et al., A combinatorial approach to create artificial homing endonucleases cleaving chosen sequences, Nucleic Acids Research, vol. 34, No. 22, Nov. 27, 2006, pp. 1-12.

Smith et al., A detailed study of the substrate specificity of a chimeric restriction enzyme, Nucleic Acids Research, 1999, pp. 674-681, vol. 27 No. 2.

Smith et al., Requirements for double-strand cleavage by chimeric restriction enzymes with zinc finger DNA-recognition domains, Nucleic Acids Research, 2000, pp. 3361-3369, vol. 28 No. 17.

Smith et al., Specific targeting of cytosine methylation to DNA sequences in vivo, Nucleic Acids Research, 2007, vol. 35, No. 3, pp. 740-754.

Spiegel et al., The structure of I-CeuI homing endonuclease: evolving asymmetric DNA recognition from a symmetric protein scaffold, Structure, May 2006, pp. 869-880, vol. 14.

Stoddard, Homing endonuclease structure and function, Quarterly Reviews of Biophysics, 2006, pp. 49-95. 47 pages.

Sussman et al., Isolation and characterization of new homing endonuclease specificities at individual target site positions, J. Mol. Biol., 2004, pp. 31-41, vol. 342. 11 pages.

Szczepek et al., Structure-based redesign of the dimerization interface reduces the toxicity of zinc-finger nucleases, Nature Biotechnology, Jul. 2007, vol. 25, No. 7, pp. 786-793.

Turmel, Monique et al. "Evolutionary Conserved and Functionally Important Residues in the I-CeuI Homing Endonuclease." Nucleic Acid Research. Apr. 1997. vol. 25, No. 13. pp. 2610-2619. 10 pages.

Tzfira et al., Site-specific integration of agrobacterium tumefaciens T-DNA via double-stranded intermediates, Plant Physiology, Nov 2003, vol. 133, pp. 1011-1023.

Tzfira et al., Towards targeted mutagenesis and gene replacement in plants, Trends in Biotechnology, Dec. 2005, pp. 567-569, vol. 23 No. 12. 3 pages.

University of Warwick, UK, Poster Abstracts Meiosis and the Causes and Consequences of Recombination, URL: http://www.biochemistry.org/meetings/postertoc.SA049/default.htm (2006) XP002501444, 2 pages.

Urnov et al., Designed transcription factors as structural, functional and therapeutic probes of chromatin in vivo, EMBO Reports, 2002, pp. 610-615, vol. 3 No. 7. 6 pages.

Urnov et al., Highly efficient endogenous human gene correction using designed zinc-finger nucleases, Nature, Jun. 2, 2005, pp. 646-651, vol. 435. 6 pages.

Van Roey et al. (2002), Catalytic domain structure and hypothesis for function of GIY-YIG intron endonuclease I-TevI, *Nature Struct. Biol.* 9: 806-811.

Vibha Srivastava et al., Cre-mediated site-specific gene integration for consistent transgene expression in rice, Plan Biotechnology Journal, (Mar. 2004) vol. 2, No. 2, pp. 169-179, XP002501441.

Wang et al., Purification, biochemical characterization and protein-DNA interactions of the I-CreI endonuclease produced in *Escherichia coli*, Nucleic Acids Research, 1997, pp. 3767-3776, vol. 25 No. 19. 10 pages.

Wehrkamp-Richter et al., Abstract P-17: I-SceI-stimulated intrachromosomal homologous recombination in maize, (2006), XP002501443, 1 page.

Wende et al., Binding, bending and cleavage of DNA substrates by the homing endonuclease PI-SceI, Nucleic Acid Res. 1996, vol. 24 No. 21: pp. 4123-4132, 10 pages.

Werner, Erik et al. "High Resolution Crystal Structure of Domain I of the Saccharomyces cerevisiae Homing Endonuclease PI-SceI." Nucelic Acid Research. Jul. 2002. vol. 30, No. 18. pp. 3962-3971. 10 pages.

Wright et al., High-frequency homologous recombination in plants mediated by zinc-finger nucleases, The Plant Journal, 2005, vol. 44; pp. 693-705, 13 pages.

* cited by examiner

SEQUENCE LISTING

```
<160> NUMBER OF SEQ ID NOS: 14

<210> SEQ ID NO 1
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Pro Lys Lys Arg Lys Val Ile Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Lys Ala Gln Ile Lys Pro Asn Gln Ser Cys Lys Phe Lys His Gln
            35                  40                  45

Leu Ser Leu Thr Phe Gln Val Thr Gln Lys Thr Gln Arg Arg Trp Phe
    50                  55                  60

Leu Asp Lys Leu Val Asp Glu Ile Gly Val Gly Tyr Val Tyr Asp Arg
65                  70                  75                  80

Gly Ser Val Ser Asp Tyr Glu Leu Ser Gln Ile Lys Pro Leu His Asn
                85                  90                  95

Phe Leu Thr Gln Leu Gln Pro Phe Leu Lys Leu Lys Gln Lys Gln Ala
                100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
        130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Leu Ser Pro Ser Gln
                165                 170                 175

Ala Ser Ser Ala Ala Ser Ser Ala Ser Ser Ser Pro Gly Ser Gly Ile
            180                 185                 190
```

```
Ser Glu Ala Leu Arg Ala Gly Ala Thr Lys Ser Lys Glu Phe Leu Leu
        195                 200                 205

Tyr Leu Ala Gly Phe Val Asp Gly Asp Gly Ser Ile Ile Ala Ser Ile
210                 215                 220

Lys Pro Arg Gln Cys Tyr Lys Phe Lys His Glu Leu Arg Leu Glu Phe
225                 230                 235                 240

Thr Val Thr Gln Lys Thr Gln Arg Arg Trp Phe Leu Asp Lys Leu Val
            245                 250                 255

Asp Glu Ile Gly Val Gly Tyr Val Asp Arg Gly Ser Val Ser Asp
            260                 265                 270

Tyr Arg Leu Ser Gln Ile Lys Pro Leu His Asn Phe Leu Thr Gln Leu
            275                 280                 285

Gln Pro Phe Leu Lys Leu Lys Gln Lys Gln Ala Asn Leu Val Leu Lys
290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
                325                 330                 335

Thr Arg Lys Thr Thr Ser Glu Thr Val Arg Ala Val Leu Asp Ser Leu
            340                 345                 350

Ser Glu Lys Lys Lys Ser Ser Pro
        355                 360

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tacgcgtacg tgtgaggtat at                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atatacctca cacgtacgcg ta                                              22

<210> SEQ ID NO 4
<211> LENGTH: 163
<212> TYPE: PRT
<213> ORGANISM: Chlamydomonas reinhardtii

<400> SEQUENCE: 4

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
```

```
                65                  70                  75                  80
Ile Lys Pro Leu His Asn Phe Leu Thr Gln Leu Gln Pro Phe Leu Lys
                        85                  90                  95
Leu Lys Gln Lys Gln Ala Asn Leu Val Leu Lys Ile Ile Trp Arg Leu
                100                 105                 110
Pro Ser Ala Lys Glu Ser Pro Asp Lys Phe Leu Glu Val Cys Thr Trp
            115                 120                 125
Val Asp Gln Ile Ala Ala Leu Asn Asp Ser Lys Thr Arg Lys Thr Thr
        130                 135                 140
Ser Glu Thr Val Arg Ala Val Leu Asp Ser Leu Ser Glu Lys Lys Lys
145                 150                 155                 160

Ser Ser Pro

<210> SEQ ID NO 5
<211> LENGTH: 22
<212> TYPE: DNA
<213> ORGANISM: Chlamydomonas reinhardtii

<400> SEQUENCE: 5
caaactgtct cacgacgttt tg                                              22

<210> SEQ ID NO 6
<211> LENGTH: 22
<212> TYPE: DNA
<213> ORGANISM: Chlamydomonas reinhardtii

<400> SEQUENCE: 6
caaaacgtcg tgagacagtt tg                                              22

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Gly Ser Val Gly Gly Leu Ser Pro Ser Gln Ala Ser Ser Ala Ala
1               5                   10                  15
Ser Ser Ala Ser Ser Pro Gly Ser Gly Ile Ser Glu Ala Leu Arg
            20                  25                  30
Ala Gly Ala Thr Lys Ser
        35

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ala Pro Lys Lys Lys Arg Lys Val
1               5

<210> SEQ ID NO 9
<211> LENGTH: 1083
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 9

```
atggcaccga agaagaagcg caaggtgatc atgaacacca agtacaacaa ggagttcctg      60
ctctacctgg cgggcttcgt ggacggggac ggctccatca aggcccagat caagccgaac     120
cagtcctgca agttcaaaca tcagctgtcg ctcaccttcc aggtcacgca agagacacag     180
cgccgttggt tcctcgacaa gctggtggac gagatcgggg tgggctacgt gtacgaccgc     240
ggcagcgtct ccgactacga gctgagccag atcaagcctc tgcacaactt cctcacccag     300
ctccagcccT tcctgaagct caagcagaag caggccaacc tcgtcctgaa gatcatcgag     360
cagctgccct ccgccaagga atccccggac aagttcctgg aggtgtgcac gtgggtcgac     420
cagatcgcgg ccctcaacga cagcaagacc cgcaagacga cctcggagac ggtgcgggcg     480
gtcctggact ccctcccagg atccgtggga ggtctatcgc catctcaggc atccagcgcc     540
gcatcctcgg cttcctcaag cccggggttca gggatctccg aagcactcag agctggagca     600
actaagtcca aggaattcct gctctacctg gcgggcttcg tggacgggga cggctccatc     660
atcgcctcga tcaagccgcg tcagtgttac aagttcaagc atgagctgag actcgagttc     720
accgtcaccc agaagacaca gcgccgttgg ttcctcgaca agctggtgga cgagatcggg     780
gtgggctacg tgtacgaccg cggcagcgtc tccgactacc gtctgtgcca gatcaagcct     840
ctgcacaact tcctgaccca gctccagccc ttcctgaagc tcaagcagaa gcaggccaac     900
ctcgtgctga gatcatcga gcagctgccc tccgccaagg aatccccgga caagttcctg     960
gaggtgtgca cctgggtgga ccagatcgcc gctctgaacg actccaagac ccgcaagacc    1020
acttccgaga ccgtccgcgc cgttctagac agtctctccg agaagaagaa gtcgtccccc    1080
tga                                                                  1083
```

<210> SEQ ID NO 10
<211> LENGTH: 1012
<212> TYPE: DNA
<213> ORGANISM: Zea mays

<400> SEQUENCE: 10

```
ttcacgcctt cacctatccc acataggtga tgagctaaga gtaaaatgta gattctctcg      60
agtactgaat attgcctgca cttttccttg cagtaaatac acctttaatc catgacgaga     120
gtccactctt tgagtccgtc ttgagattct tccattgatc atacaacatg acctcgaagt     180
cctgatggag aacaacttat ataattaaaa ctacaataca gaaagttcct gacaattaaa     240
accttTggtg gtggcatgcc gtaggttaaa aaaaatagat aatgacaaca caactggaga     300
cacgctcttt gccgagtgct cacacgtttg ctgagagcga gcactcggca aatatatgat     360
ttgccgaata ccaccctcct cggcaaaaca atacactagg caaaaggta gtttcccatc     420
accatgatgc ccgccgttaa tgtaccttct atgccgagta tgttggcgct cagcaaagag     480
atcgttaccg gcgtttgttt caccaagagc tctttgacga gtgtggcaca cgacaaaacc     540
ttttgccgag tgtaattagt cgtttgccaa gtgactggtg cagttggcaa aggagtcgtt     600
tattatgtgt gggcaaaatg atatatggtg ccagttaggg ctagcaaatt aaagggggggg     660
gggggggggt taggttgaag aaggtgacga gtaataaggt ctcggacggc cgcgcgcata     720
tatatcagat ccgatccaat ggcacacggt gcaaacgaaa agcacgaaat ttccaccagc     780
ttaattaggg agagaaaaat agagcaccag ctgatgagtg aatgaatgag atagacggga     840
cacagagggt ccagcaggct agcctactct ggccgcccta aatagaagtc agtgccgtga     900
```

```
cgacgcgcaa acttcttttg atcggctgcg gaaataatat actgtaacga tttacgcacc    960
tgctgggaat tgtaccgtac gtgccccggc ggaggatata tatacctcac ac           1012
```

<210> SEQ ID NO 11
<211> LENGTH: 1000
<212> TYPE: DNA
<213> ORGANISM: Zea mays

<400> SEQUENCE: 11

```
acgtacgcgt acgcgtatat atacgtgcgc tgctactcat ttgcgcgcgg gaatacagct     60
cagtctgctc tgcctctgct gcaggatgta catgcataca tgcgcaggtg caaataaagt    120
ctacgcgcgg gcaagcccct ggcgtagctg gccatatga ctgagatcac gcctcatggt    180
catggaacga acaccgcgt ccggccgggc tgccctggc gtcacgcggg aggcactgct    240
agcgttagcg tacgtaccca ccgtctcgta cagcaccgca gggagaggag agcgatgcaa    300
tgcacatgta cagcatccgc atcatgcata gatactcata tcttcaaggc cacacatgca    360
gcagtgtcgt acgctacgtt gtttcaacgg aggaggagga tacatacata gatacccata    420
gccagcctag catatagcag atagcatacg gactcccggg tgaggaaaaa tggagggcga    480
accaaaccaa ccacaaagaa gcagcagcag cagcagcagc agctgcggct gctatcacca    540
ctcaccaact ccaattaaag atctctctct ctctctctac tggccggccc tgtcagtgcc    600
agcgcccggt ttgttgctag ctgagctgcg ggcgtcgctc ttagatatag cccaaaactc    660
actccaccac cactcgttcc atggaaccct agaccaaaag tactcgcgct ctcggctctc    720
gctctcgccc tctccctctc cgcagcaaaa gagatccggc cggccgagaa gggcgcgcgc    780
tagctgcccg gctactagct ggcgcccgcc cgcgcatata tctgtgtcat cgccatcacc    840
cacaccatgg cccggccggc caacaccgcc gtattagctc tgtctgtcgc tcgtccacct    900
gcgaccgact gagcgatcga tctccaccga gctctccgct aagcgctgtc cttgccgccg    960
tcctcccctc cgtcccctac gcatccattt ccgtgtgctc                         1000
```

<210> SEQ ID NO 12
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Ala Pro Lys Lys Lys Arg Lys Val Ile Met Asn Thr Lys Tyr Asn
1               5                   10                  15

Lys Glu Phe Leu Leu Tyr Leu Ala Gly Phe Val Asp Gly Asp Gly Ser
            20                  25                  30

Ile Lys Ala Gln Ile Lys Pro Asn Gln Ser Cys Lys Phe Lys His Gln
        35                  40                  45

Leu Ser Leu Thr Phe Gln Val Thr Gln Lys Thr Gln Arg Arg Trp Phe
    50                  55                  60

Leu Asp Lys Leu Val Asp Glu Ile Gly Val Gly Tyr Val Tyr Asp Arg
65                  70                  75                  80

Gly Ser Val Ser Asp Tyr Glu Leu Ser Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125
```

```
Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                165                 170                 175

Ala Ser Ser Ala Ala Ser Ser Ala Ser Ser Pro Gly Ser Gly Ile
            180                 185                 190

Ser Glu Ala Leu Arg Ala Gly Ala Thr Lys Ser Lys Glu Phe Leu Leu
            195                 200                 205

Tyr Leu Ala Gly Phe Val Asp Gly Asp Gly Ser Ile Ile Ala Ser Ile
    210                 215                 220

Lys Pro Arg Gln Cys Tyr Lys Phe Lys His Glu Leu Arg Leu Thr Phe
225                 230                 235                 240

Thr Val Thr Gln Lys Thr Gln Arg Arg Trp Phe Leu Asp Lys Leu Val
                245                 250                 255

Asp Glu Ile Gly Val Gly Tyr Val Tyr Asp Arg Gly Ser Val Ser Asp
            260                 265                 270

Tyr Arg Leu Ser Gln Ile Lys Pro Leu His Asn Phe Leu Thr Gln Leu
    275                 280                 285

Gln Pro Phe Leu Lys Leu Lys Gln Lys Gln Ala Asn Leu Val Leu Lys
290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
                325                 330                 335

Thr Arg Lys Thr Thr Ser Glu Thr Val Arg Ala Val Leu Asp Ser Leu
            340                 345                 350

Ser Glu Lys Lys Lys Ser Ser Pro
    355                 360

<210> SEQ ID NO 13
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Pro Lys Lys Arg Lys Val Ile Met Asn Thr Lys Tyr Asn
1               5                   10                  15

Lys Glu Phe Leu Leu Tyr Leu Ala Gly Phe Val Asp Gly Asp Gly Ser
                20                  25                  30

Ile Lys Ala Gln Ile Lys Pro Asn Gln Ser Cys Lys Phe Lys His Gln
            35                  40                  45

Leu Ser Leu Thr Phe Gln Val Thr Gln Lys Thr Gln Arg Arg Trp Phe
        50                  55                  60

Leu Asp Lys Leu Val Asp Glu Ile Gly Val Gly Tyr Val Tyr Asp Arg
65                  70                  75                  80

Gly Ser Val Ser Asp Tyr Ile Leu Cys Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125
```

```
Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                165                 170                 175

Ala Ser Ser Ala Ala Ser Ser Ala Ser Ser Pro Gly Ser Gly Ile
            180                 185                 190

Ser Glu Ala Leu Arg Ala Gly Ala Thr Lys Ser Lys Glu Phe Leu Leu
            195                 200                 205

Tyr Leu Ala Gly Phe Val Asp Gly Asp Gly Ser Ile Ile Ala Ser Ile
            210                 215                 220

Lys Pro Arg Gln Cys Tyr Lys Phe Lys His Glu Leu Arg Leu Thr Phe
225                 230                 235                 240

Thr Val Thr Gln Lys Thr Gln Arg Arg Trp Phe Leu Asp Lys Leu Val
                245                 250                 255

Asp Glu Ile Gly Val Gly Tyr Val Tyr Asp Arg Gly Ser Val Ser Asp
                260                 265                 270

Tyr Arg Leu Ser Gln Ile Lys Pro Leu His Asn Phe Leu Thr Gln Leu
            275                 280                 285

Gln Pro Phe Leu Lys Leu Lys Gln Lys Gln Ala Asn Leu Val Leu Lys
            290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
                325                 330                 335

Thr Arg Lys Thr Thr Ser Glu Thr Val Arg Ala Val Leu Asp Ser Leu
            340                 345                 350

Ser Glu Lys Lys Lys Ser Ser Pro
            355                 360

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```

RATIONALLY-DESIGNED MEGANUCLEASE VARIANTS OF LIG-34 AND I-CREI FOR MAIZE GENOME ENGINEERING

CROSS-REFERENCE SECTION

This application is a Continuation of International Application PCT/US2009/035719 filed Mar. 2, 2009, which claims the benefit of U.S. Provisional Application No. 61/035,613, filed Mar. 11, 2008, the entire disclosures of which are incorporated by reference herein.

FIELD OF THE INVENTION

The invention relates to the field of molecular biology and recombinant nucleic acid technology. In particular, the invention relates to a rationally-designed, non-naturally-occurring meganuclease with altered DNA recognition sequence specificity which recognizes and cleaves a unique DNA site in the maize genome. The invention also relates to methods of producing engineered maize plants using such meganucleases.

BACKGROUND OF THE INVENTION

Genome engineering requires the ability to insert, delete, substitute and otherwise manipulate specific genetic sequences within a genome, and has numerous therapeutic and biotechnological applications. The development of effective means for genome modification remains a major goal in gene therapy, agrotechnology, and synthetic biology (Porteus et al. (2005), *Nat. Biotechnol.* 23: 967-73; Tzfira et al. (2005), *Trends Biotechnol.* 23: 567-9; McDaniel et al. (2005), *Curr. Opin. Biotechnol.* 16: 476-83). A common method for inserting or modifying a DNA sequence involves introducing a transgenic DNA sequence flanked by sequences homologous to the genomic target and selecting or screening for a successful homologous recombination event. Recombination with the transgenic DNA occurs rarely but can be stimulated by a double-stranded break in the genomic DNA at the target site. Numerous methods have been employed to create DNA double-stranded breaks, including irradiation and chemical treatments. Although these methods efficiently stimulate recombination, the double-stranded breaks are randomly dispersed in the genome, which can be highly mutagenic and toxic. At present, the inability to target gene modifications to unique sites within a chromosomal background is a major impediment to successful genome engineering.

One approach to achieving this goal is stimulating homologous recombination at a double-stranded break in a target locus using a nuclease with specificity for a sequence that is sufficiently large to be present at only a single site within the genome (see, e.g., Porteus et al. (2005), *Nat. Biotechnol.* 23: 967-73). The effectiveness of this strategy has been demonstrated in a variety of organisms using chimeric fusions between an engineered zinc finger DNA-binding domain and the non-specific nuclease domain of the FokI restriction enzyme (Porteus (2006), *Mol Ther* 13: 438-46; Wright et al. (2005), *Plant J.* 44: 693-705; Urnov et al. (2005), *Nature* 435: 646-51). Although these artificial zinc finger nucleases stimulate site-specific recombination, they retain residual non-specific cleavage activity resulting from under-regulation of the nuclease domain and frequently cleave at unintended sites (Smith et al. (2000), *Nucleic Acids Res.* 28: 3361-9). Such unintended cleavage can cause mutations and toxicity in the treated organism (Porteus et al. (2005), *Nat. Biotechnol.* 23: 967-73).

A group of naturally-occurring nucleases which recognize 15-40 base-pair cleavage sites commonly found in the genomes of plants and fungi may provide a less toxic genome engineering alternative. Such naturally-occurring "meganucleases" or "homing endonucleases" are frequently associated with parasitic DNA elements, such as group I self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Meganucleases are commonly grouped into four families: the LAGLIDADG (SEQ ID NO: 15)family, the GIY-YIG family, the His-Cys box family and the HNH family. These families are characterized by structural motifs, which affect catalytic activity and recognition sequence. For instance, members of the LAGLIDADG(SEQ ID NO: 15) family are characterized by having either one or two copies of the conserved LAGLIDADG (SEQ ID NO: 15) motif (see Chevalier et al. (2001), *Nucleic Acids Res.* 29(18): 3757-3774). The LAGLIDADG (SEQ ID NO: 15) meganucleases with a single copy of the LAGLIDADG (SEQ ID NO: 15) motif form homodimers, whereas members with two copies of the LAGLIDADG (SEQ ID NO: 15) motif are found as monomers. Similarly, the GIY-YIG family members have a GIY-YIG module, which is 70-100 residues long and includes four or five conserved sequence motifs with four invariant residues, two of which are required for activity (see Van Roey et al. (2002), *Nature Struct. Biol.* 9: 806-811). The His-Cys box meganucleases are characterized by a highly conserved series of histidines and cysteines over a region encompassing several hundred amino acid residues (see Chevalier et al. (2001), *Nucleic Acids Res.* 29(18): 3757-3774). In the case of the NHN family, the members are defined by motifs containing two pairs of conserved histidines surrounded by asparagine residues (see Chevalier et al. (2001), *Nucleic Acids Res.* 29(18): 3757-3774). The four families of meganucleases are widely separated from one another with respect to conserved structural elements and, consequently, DNA recognition sequence specificity and catalytic activity.

Naturally-occurring meganucleases, primarily from the LAGLIDADG (SEQ ID NO: 15) family, have been used to effectively promote site-specific genome modification in plants, yeast, *Drosophila*, mammalian cells and mice, but this approach has been limited to the modification of either homologous genes that conserve the meganuclease recognition sequence (Monnat et al. (1999), *Biochem. Biophys. Res. Commun.* 255: 88-93) or to pre-engineered genomes into which a recognition sequence has been introduced (Rouet et al. (1994), *Mol. Cell. Biol.* 14: 8096-106; Chilton et al. (2003), *Plant Physiol.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622).

Systematic implementation of nuclease-stimulated gene modification requires the use of engineered enzymes with customized specificities to target DNA breaks to existing sites in a genome and, therefore, there has been great interest in engineering meganucleases to promote gene modifications at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62).

The meganuclease I-CreI from *Chlamydomonas reinhardtii* is a member of the LAGLIDADG (SEQ ID NO: 15) family which recognizes and cuts a 22 base-pair recognition sequence in the chloroplast chromosome, and which presents an attractive target for meganuclease redesign. The wild-type enzyme is a homodimer in which each monomer makes direct contacts with 9 base pairs in the full-length recognition sequence. Genetic selection techniques have been used to identify mutations in I-CreI that alter base preference at a single position in this recognition sequence (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9) or, more recently, at three positions in the recognition sequence (Arnould et al. (2006), *J. Mol. Biol.* 355: 443-58). The I-CreI protein-DNA interface contains nine amino acids that contact the DNA bases directly and at least an additional five positions that can form potential contacts in mutant interfaces. The size of this interface imposes a combinatorial complexity that is unlikely to be sampled adequately in sequence libraries constructed to select for enzymes with drastically altered cleavage sites.

There remains a need for nucleases that will facilitate precise modification of a genome by cleaving any desired genomic sequence, including sequences not cleaved by naturally-occurring homing endonucleases. This is particularly true of the agriculture industry in which the production of genetically modified crop lines is significantly hindered by the current inability to target the insertion or removal of nucleic acids from specific regions of the genome. The present invention provides, inter alia, an engineered meganucleases which recognize a unique DNA sequence found in the *Zea mays* (maize) genome and methods for using these engineered meganucleases to precisely target the insertion of nucleic acids into the maize genome.

SUMMARY OF THE INVENTION

The present invention relates to certain engineered meganucleases ("LIG-34 meganucleases") which recognize and cut a 22 basepair DNA sequence found in the genome of *Zea mays* (maize). The invention provides a composition comprising a LIG34 meganuclease, a maize plant comprising an exogenous DNA sequence in its chromosome, as well as methods that use LIG34 meganucleases to target the insertion of nucleic acids into a specific locus in the maize genome.

In one aspect, the invention provides a rationally-designed meganuclease having the amino acid sequence of SEQ ID NO: 1. In another aspect, the invention provides a rationally-designed meganuclease having the amino acid sequence of SEQ ID NO: 12. In yet another aspect, the invention provides a rationally-designed meganuclease having the amino acid sequence of SEQ ID NO: 13.

In one aspect, the invention provides a rationally-designed meganuclease having at least 85% sequence identity to the amino acid sequence of SEQ ID NO: 1, SEQ ID NO:12 and/or SEQ ID NO: 13 which recognizes and cleaves the double-stranded DNA sequence of SEQ ID NO: 2 and SEQ ID NO:3.

In another aspect, the invention provides a method for the production of a recombinant maize plant in which a sequence of interest is integrated the maize genome, the method comprising transforming a maize cell or embryo with: (a) a first DNA molecule comprising:
a DNA sequence encoding a meganuclease having at least 85% sequence identity to the amino acid sequence of SEQ ID NO: 1, SEQ ID NO: 12 and/or SEQ ID NO:13 which recognizes and cleaves the double-stranded DNA sequence of SEQ ID NO: 2 and SEQ ID NO:3; and a promoter suitable for the expression of such a meganuclease in maize; and (b) a second DNA molecule comprising a sequence of interest.

In yet another aspect, the invention provides a method for the production of a recombinant maize plant in which a sequence of interest is integrated the maize genome, the method comprising transforming a maize cell or embryo with: (a) a first DNA molecule comprising: a DNA sequence encoding a meganuclease having at least 85% sequence identity to the amino acid sequence of SEQ ID NO: 1, SEQ ID NO:12 and/or SEQ ID NO:13 which recognizes and cleaves the double-stranded DNA sequence of SEQ ID NO: 2 and SEQ ID NO:3; and a promoter suitable for the expression of such a meganuclease in maize; and (b) a second DNA molecule comprising: a sequence of interest flanked on one side by a DNA sequence with homology to 50-900 consecutive base pairs of SEQ ID NO: 10 and flanked on the other side by a DNA sequence with homology to 50-900 consecutive base pairs of SEQ ID NO: 11.

The sequence of interest can be flanked on at least one side by the first nine nucleotides from the meganuclease recognition sequence of SEQ ID NO: 2 or SEQ ID NO: 3. The maize cell or embryo can be transformed with a molecule comprising the first DNA molecule and the second DNA molecule. The maize cell or embryo can be transformed with a molecule comprising the first DNA molecule and the second DNA molecule and wherein SEQ ID NO: 2 or SEQ ID NO: 3 is located between the DNA sequence encoding the meganuclease and the sequence of interest.

In one aspect, the invention provides a maize plant with a chromosome comprising a composite sequence, the composite sequence comprising: a sequence of interest; a first sequence comprising 50-900 base pairs from SEQ ID NO: 10 immediately upstream of the sequence of interest; and a second sequence comprising 50-900 base pairs from SEQ ID NO: 11 immediately downstream of the sequence of interest. The sequence of interest can comprise an exogenous gene.

In some embodiments of the maize plant, the composite sequence is free of retroviral sequences, *Agrobacterium tumefaciens* sequences and/or transposon sequences. In some embodiments, the maize plant has a single composite sequence in said chromosome.

In some embodiments of the maize plant, the 3' nucleotide of the first sequence corresponds to a nucleotide selected from the group consisting of nucleotides 950-961 of SEQ ID NO: 10. In some embodiments of the maize plant, the 5' nucleotide of the second sequence corresponds to a nucleotide selected from the group consisting of nucleotides 1-11 of SEQ ID NO: 11.

In one aspect, the invention provides a maize plant having a sequence of interest inserted in its chromosome, wherein the sequence of interest is inserted into SEQ ID NO: 2 and SEQ ID NO: 3.

In some embodiments, the sequence of interest is inserted only once into said chromosome. The sequence of can interest can comprise an exogenous gene.

hydrogen bonds and hydrophobic contacts to DNA bases. Arrows: residues that interact with the DNA backbone and influence cleavage activity.

Figure 2:
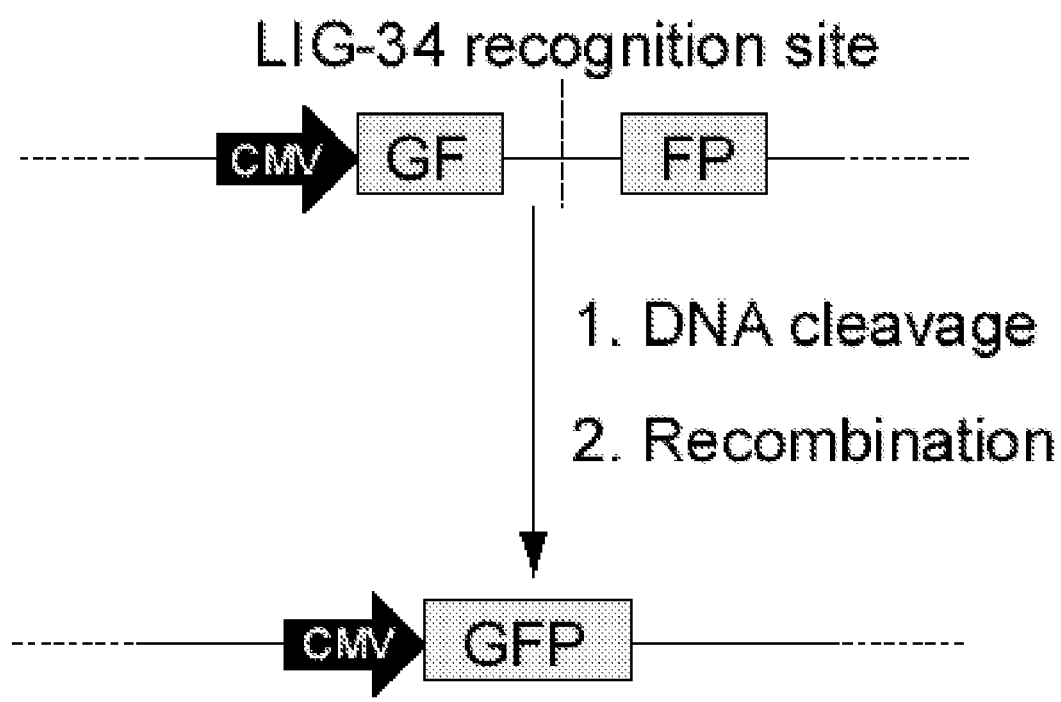

FIG. 2 is a schematic of a direct-repeat recombination assay used to evaluate the LIG-34 meganucleases. To perform this assay, as described in detail in Example 2, a defective GFP reporter gene was stably integrated into the chromosomal DNA of a human (HEK-293) cell-line. The gene is interrupted by a LIG-34 recognition site which is flanked by ~250 base pairs of directly repeated sequence of the GFP gene. This reporter cell-line is then transfected with a mammalian expression vector carrying a LIG-34 meganuclease gene and in vivo cleavage of the LIG-34 site by the meganuclease stimulates homologous recombination between direct repeats of the GFP gene, which results in a functional GFP (GFP+) coding sequence. GFP+ cells can then be counted by flow cytometry.

Figure 3:
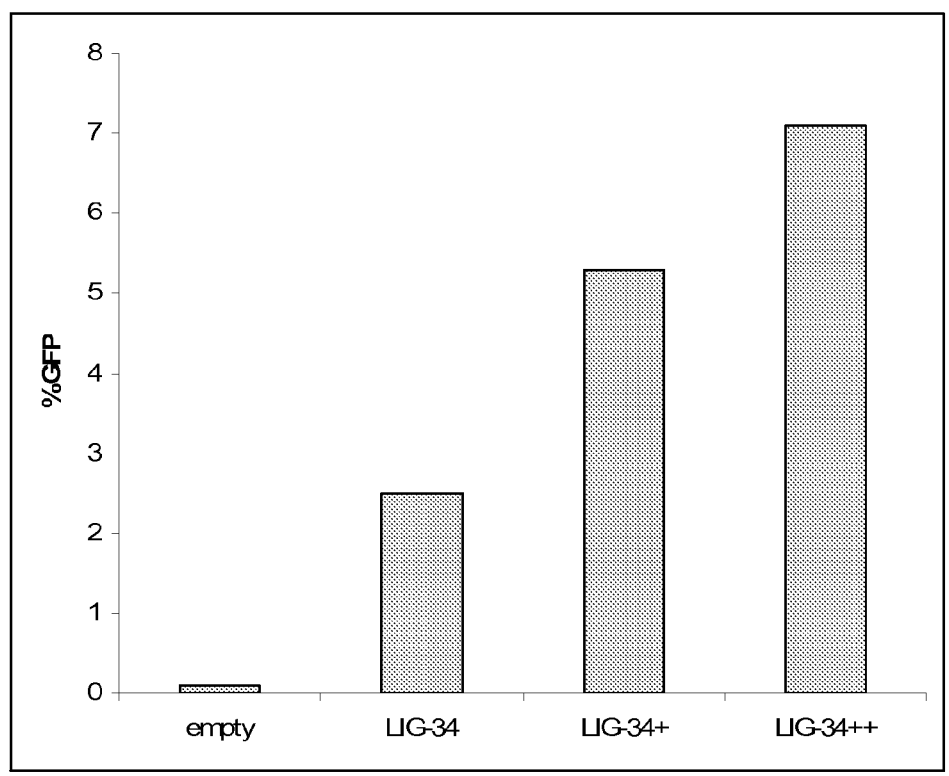

FIG. 3 is a bar graph representation of the results of the assay described in FIG. 2 to evaluate the LIG-34, LIG-34+, and LIG-34++ meganucleases. The three meganucleases produced GFP+ cells with frequencies of 2.5%, 5.3%, and 7.1%, respectively, while an empty expression vector yielded <0.1% GFP+ cells.

DETAILED DESCRIPTION OF THE INVENTION 1.1 Introduction

The present invention provides engineered meganucleases which specifically recognize and cleave a 22 bp, double-stranded DNA sequence found in the maize genome, that has the sequence shown in SEQ ID NO: 2 and SEQ ID NO: 3, and which is referred to herein as the "LIG-34 recognition site." These meganucleases are produced, in part, in accordance with the methods disclosed in WO 2007/047859. Examples of such meganucleases include those designated herein as "LIG-34" (SEQ ID NO: 1), "LIG-34+" (SEQ ID NO: 12) and "LIG-34++" (SEQ ID NO: 13). The disclosure of WO 2007/047859, which is incorporated herein by reference, describes a method for the production of meganucleases derived from the natural I-CreI homing endonuclease, but that recognize DNA sequences that differ from the sequence recognized by wild-type I-CreI. The LIG-34, LIG-34+, LIG-34++ meganucleases, as well as other meganucleases produced according to the methods disclosed in WO 2007/047859, and that recognize and cleave the LIG-34 recognition site, are collectively referred to herein as "LIG34 meganucleases."

The LIG-34 meganucleases can be used for cleaving a unique DNA site in the genome of Zea mays and thereby enable gene insertion at that site in the genome. This invention will have a significant impact on the agriculture industry as it allows seed producers to generate transgenic maize plants in which trait genes of agronomic value (e.g., herbicide resistance genes, insect resistance genes, drought tolerance genes, disease resistance genes, and genes affecting yield or fertility) are inserted precisely at the LIG-34 recognition site. Although methods for incorporating transgenes into the maize genome are well known in the art (e.g., Agrobacterium-mediated transformation, particle-bombardment, "whiskers" transformation, and lipofection) these methods integrate transgenes at more-or-less random locations in the genome. The ability to target transgene insertion to the LIG-34 recognition site has numerous advantages over these existing methods. First, it enables transgenes to be inserted into a region of the genome with known gene expression characteristics. Second, it enables the repeated targeting of trait genes to the same genomic locus, which will accelerate regulatory approval of subsequent genetically modified maize products following a first approval. Lastly, it enables multiple genes to be inserted adjacent to one another in the same region of the genome so that they are genetically linked and will consistently co-segregate throughout subsequent breedings.

Thus, in one embodiment, this invention provides a LIG-34 meganuclease. In another embodiment, it provides methods for using a LIG-34 meganuclease to insert transgenes into the maize genome at the LIG-34 recognition site.

1.2 References and Definitions

The patent and scientific literature referred to herein establishes knowledge that is available to those of skill in the art. The issued U.S. patents, allowed applications, published foreign applications, and references, including GenBank database sequences, that are cited herein are hereby incorporated by reference to the same extent as if each was specifically and individually indicated to be incorporated by reference.

As used herein, the term "meganuclease" refers to a naturally-occurring homing endonuclease that binds double-stranded DNA at a recognition sequence that is greater than 12 base pairs and encompasses the corresponding intron insertion site. Naturally-occurring meganucleases can be monomeric (e.g., I-SceI) or dimeric (e.g., I-CreI). The term meganuclease, as used herein, can be used to refer to monomeric meganucleases, dimeric meganucleases, or to the monomers which associate to form a dimeric meganuclease.

As used herein, the term "rationally-designed" means non-naturally occurring and/or genetically engineered. The rationally-designed meganucleases of the invention differ from wild-type or naturally-occurring meganucleases in their amino acid sequence or primary structure, and may also differ in their secondary, tertiary or quaternary structure. In addition, the rationally-designed meganucleases of the invention also differ from wild-type or naturally-occurring meganucleases in recognition sequence-specificity and/or activity.

As used herein, with respect to a protein, the term "recombinant" means having an altered amino acid composition as a result of the application of genetic engineering techniques to nucleic acids which encode the protein, and cells or organisms which express the protein. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous different host, is not considered recombinant.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term "wild-type" refers to any naturally-occurring form of a meganuclease. The term "wild-type" is not intended to mean the most common allelic variant of the enzyme in nature but, rather, any allelic variant found in nature. Wild-type meganucleases are distinguished from recombinant or non-naturally-occurring meganucleases.

As used herein, the term "recognition sequence half-site" or simply "half site" means a nucleic acid sequence in a double-stranded DNA molecule which is recognized by a monomer of a mono-LAGLIDADG (SEQ ID NO: 15) meganuclease or by one LAGLIDADG (SEQ ID NO: 15) subunit of a di-LAGLIDADG meganuclease.

As used herein, the term "recognition sequence" refers to a pair of inverted half-sites separated by four base pairs, which is bound and cleaved by either a mono-LAGLIDADG (SEQ ID NO: 15) meganuclease dimer or a di-LAGLIDADG (SEQ ID NO: 15) meganuclease monomer. In the case of I-CreI, the recognition sequence half-site of each monomer spans 9 base pairs, and the two half-sites are separated by four base pairs, designated $N_1$ through $N_4$, which are not recognized specifically. Thus, the combined recognition sequence of the I-CreI meganuclease dimer normally spans 22 base pairs, including the 9 base pairs 5' of the central $N_1$-$N_4$ bases on the sense strand, which are designated −9 through −1, the central $N_1$-$N_4$ base pairs, and the 9 base pairs 3' of the central $N_1$-$N_4$ bases on the sense strand, which are designated −1 through −9.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences.

As used herein, the term "palindromic" refers to a recognition sequence consisting of inverted repeats of identical half-sites. In this case, however, the palindromic sequence need not be palindromic with respect to the four central nucleotide pairs, which are not contacted by the enzyme. In the case of dimeric meganucleases, palindromic DNA sequences are recognized by homodimers in which the two monomers make contacts with identical half-sites.

As used herein, the term "pseudo-palindromic" refers to a recognition sequence consisting of inverted repeats of non-identical or imperfectly palindromic half-sites. In this case, the pseudo-palindromic sequence not only need not be palindromic with respect to the four central nucleotide pairs, but also can deviate from a palindromic sequence between the two half-sites. Pseudo-palindromic DNA sequences are typical of the natural DNA sites recognized by wild-type homodimeric meganucleases in which two identical enzyme monomers make contacts with different half-sites.

As used herein, the term "non-palindromic" refers to a recognition sequence composed of two unrelated half-sites of a meganuclease. In this case, the non-palindromic sequence need not be palindromic with respect to either the four central nucleotide pairs or the two monomer half-sites. Non-palindromic DNA sequences are recognized by either highly degenerate meganucleases (e.g., I-CeuI) or by heterodimers of meganuclease monomers that recognize non-identical half-sites.

As used herein, the term "activity" refers to the rate at which a meganuclease of the invention cleaves a particular recognition sequence. Such activity is a measurable enzymatic reaction, involving the hydrolysis of phosphodiester bonds of double-stranded DNA. The activity of a meganuclease acting on a particular DNA substrate is affected by the affinity or avidity of the meganuclease for that particular DNA substrate which is, in turn, affected by both sequence-specific and non-sequence-specific interactions with the DNA.

As used herein, the term "LIG-34 recognition site" refers to a region of the maize genome approximately 1200 basepairs 5' of the LIGULESS1 gene (genbank accession #AF451895) which contains the 22 bp DNA sequence recognized by the LIG-34 meganuclease (SEQ ID NO: 2 and SEQ ID NO: 3).

2. The LIG-34 Meganuclease

Figure 1:
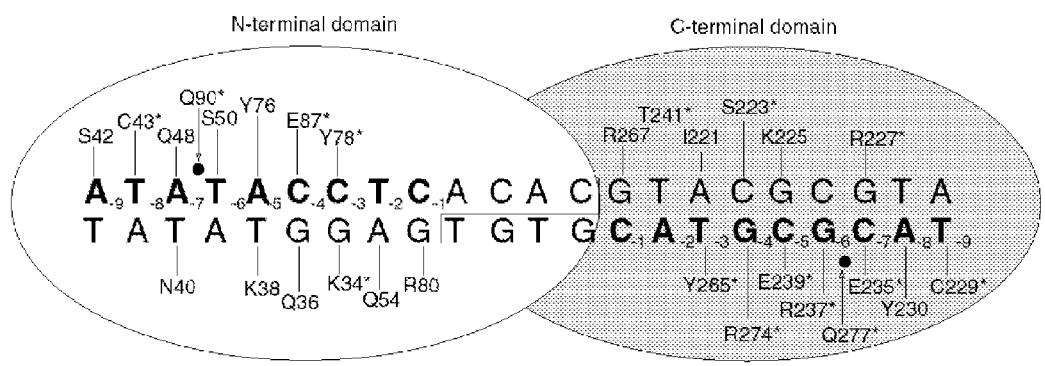
FIG. 1 illustrates the interactions between the LIG-34 meganuclease and its double-stranded recognition sequence found in the maize genome. This schematic representation depicts the recognition sequence (SEQ ID NO: 2 and SEQ ID NO: 3), shown as unwound for illustration purposes only, bound by the LIG-34 meganuclease. The N- and C-terminal domains of LIG-34 are shown as two ovals. The bases of each DNA half-site are numbered −1 through −9, and the amino acid residues of LIG-34 which form the recognition surface are indicated by one-letter amino acid designations and numbers indicating residue position. Amino acids with asterisks are mutant relative to wild-type I-CreI. Solid black lines.

The LIG-34 meganuclease is a derivative of I-CreI that is genetically engineered with respect to its DNA cleavage specificity in accordance with the method disclosed in WO/2007/047859. The amino acid substitutions that were introduced into the LIG-34 meganuclease for the purpose of altering DNA cleavage specificity are diagrammed in FIG. 1 and listed in Table 1. Because LIG-34 is a single-chain heterodimeric meganuclease whereas I-CreI is a homodimer and because the LIG-34 meganuclease has an N-terminal nuclease localization signal (as discussed below) the amino acid numbering differs from wild-type I-CreI. Table 1, therefore, also lists the corresponding DNA contacting residue in the amino acid sequence of wild-type I-CreI (SEQ ID NO: 4).

TABLE 1

Mutations in LIG-34 which alter DNA-cleavage specificity relative to wild-type I-CreI.

| LIG-34 (N-terminal domain) | LIG-34 (C-terminal domain) | wild-type I-CreI |
|---|---|---|
| K34 | | I24 |
| | S223 | Q26 |
| | R227 | N30 |
| | C229 | S32 |
| C43 | | Y33 |
| | E235 | Q38 |
| | R237 | S40 |
| | E239 | T42 |
| | T241 | Q44 |
| Y78 | Y265 | R68 |
| E87 | R274 | I77 |

In addition to the amino acid substitutions listed in Table 1 which were designed to control DNA-cleavage specificity, LIG-34 endonucleases may incorporate additional amino acid substitutions intended to increase the overall cleavage activity of the meganuclease (Table 2). In the cases of I87 and T239, the activity of the LIG-34 meganuclease is increased by reverting negatively-charged amino acids, which were introduced to alter cleavage specificity (E87 and E239, see Table 1) back to the wild-type amino acid. The net effect is a reduction in the overall specificity of the endonuclease, but an increase in endonuclease activity due to the removal of negative charges (which repulse the negatively charged DNA and, thereby, reduce DNA-binding affinity) from the protein-DNA interface. In the cases of Q90 and Q277, the incorporation of glutamine at these amino acid positions, whereas wild-type I-CreI has glutamic acid in the corresponding position, eliminates electrostatic repulsion between the negatively-charged glutamic acid sidechain and the negatively-charged DNA. The effect of this pair of substitutions is that the overall DNA binding affinity of the engineered meganuclease is increased with a corresponding increase in the cleavage activity. In the cases of C89 and C276, the introduction of cysteine at these positions, whereas wild-type I-CreI has a serine in the corresponding position, increases the endonuclease affinity for DNA (and, hence, DNA cleavage activity), presumably through a favorable van der Waals interaction with the DNA backbone. The remaining amino acid substitutions listed in Table 2 convert an uncharged amino acid (Y66, I81, and/or P113) to a positively-charged amino acid (K or R). All of these substitutions are believed to introduce favorable electrostatic interactions between the positively-charged amino acid sidechain and the negatively-charged phosphate backbone of the DNA. Again, the net effect is to increase the DNA-binding affinity which increases cleavage activity.

TABLE 2

Mutations in LIG-34 which increase DNA-cleavage activity

| LIG-34 (N-terminal domain) | LIG-34 (C-terminal domain) | wild-type I-CreI |
|---|---|---|
|  | T239 | T42 |
| K76/R76 | K263/R263 | Y66 |
| I87 |  | I77 |
| C89 | C276 | S79 |
| Q90 | Q277 | E80 |
| K91/R91 | K278/R278 | I81 |
| K123/R123 | K310/R310 | P113 |

The introduction of some or all of the modifications listed in Table 2 is useful to restore the level of cleavage activity that is lost upon introducing the mutations listed in Table 1 so that the LIG-34 meganuclease maintains the ability to cleave DNA at a rate that is comparable to wild-type I-CreI. Thus, the invention provides a family of engineered meganucleases which cleave the LIG-34 recognition sequence (SEQ ID NO: 2 and SEQ ID NO: 3), but do so with varying degrees of endonuclease activity and/or specificity due to different combinations of the mutations listed in Table 2. For example, one preferred embodiment of LIG-34 is SEQ ID NO: 1, which incorporates the mutations listed in Table 1 as well as Q90 and Q277 from Table 2. A second preferred embodiment is SEQ ID NO: 12, referred to as "LIG-34+", which incorporates the mutations listed in Table 1 as well as Q90, Q277, and T239 (which is a reversion back to a wild-type amino acid). LIG-34+ cleaves the LIG-34 recognition sequence more efficiently in vitro as well as in planta relative to SEQ ID NO: 1, but has slightly reduced specificity relative to SEQ ID NO: 1. A third preferred embodiment is SEQ ID NO: 13, referred to as "LIG-34++" which incorporates the mutations listed in Table 1 as well as Q90, Q277, C89, I87, and T239 (the latter two are reversions back to a wild-type amino acid). LIG-34++ cleaves the LIG-34 recognition sequence more efficiently in vitro and in planta than SEQ ID NO:1 and SEQ ID NO: 12, but has reduced specificity relative to SEQ ID NO:1 and SEQ ID NO: 12.

As discussed in WO/2007/047859, wild-type I-CreI binds to and cleaves DNA as a homodimer. As a consequence, the natural recognition sequence for I-CreI (SEQ ID NO: 5, SEQ ID NO: 6) is pseudo-palindromic. The LIG-34 recognition sequence (SEQ ID NO: 2, SEQ ID NO: 3), however, is non-palindromic. This necessitates the use of an engineered meganuclease heterodimer comprising a pair of subunits each of which recognizes one half-site within the full-length recognition sequence. In the case of LIG-34, the two engineered meganuclease monomers are physically linked to one another using an amino acid linker to produce a single-chain heterodimer. This linker comprises amino acids 166-204 (SEQ ID NO: 7) of LIG-34. The linker sequence joins an N-terminal meganuclease subunit terminated at L165 (corresponding to L155 of wild-type I-CreI) with a C-terminal meganuclease subunit starting at K204 (corresponding to K7 of wild-type I-CreI). The benefits of physically linking the two meganuclease monomers using this novel linker are twofold: first, it ensures that the meganuclease monomers can only associate with one another (heterodimerize) to cut the non-palindromic LIG-34 recognition sequence rather than also forming homodimers which can recognize palindromic or pseudopalindromic DNA sites that differ from the LIG-34 recognition sequence. Second, the physical linking of meganuclease monomers obviates the need to express two monomers simultaneously in the same cell to obtain the desired heterodimer. This significantly simplifies vector construction in that it only requires a single gene expression cassette.

Lastly, the LIG-34 meganuclease incorporates an N-terminal nuclear localization signal (NLS, SEQ ID NO: 7) derived from the mammalian SV40 virus. This peptide leader sequence was added to direct the LIG-34 meganuclease to the nucleus of a maize cell. The use of the SV40 NLS sequence is common in the art.

The LIG-34 meganucleases of SEQ ID NO: 1, SEQ ID NO: 12, and SEQ ID NO: 13 have been evaluated using an in vitro DNA cleavage assay and were found to cleave the LIG-34 recognition sequence with efficiency comparable to or better than wild-type I-CreI, as shown in Example 1.

3. Methods of Producing Recombinant Maize Using the LIG-34 Meganuclease

Aspects of the present invention further provide methods for producing recombinant, transgenic or otherwise genetically-modified maize cells and plants using LIG-34 (uses for LIG-34 are also discussed in WO 2009/006297). Thus, in one embodiment, the LIG-34 meganuclease is used to cause a double-stranded break at the LIG-34 recognition site to allow for precise insertion(s) of a sequence of interest into that site by homologous recombination. In another embodiment, the LIG-34 meganuclease is used to cause a double-stranded break at the LIG-34 recognition site to allow for precise insertion(s) of a sequence of interest into that site by non-homologous end joining.

As used herein, the term "sequence of interest" means any DNA sequence that can be inserted into the maize genome. Sequences of interest will typically be genes that confer commercially valuable traits to maize plants (e.g., genes that confer herbicide resistance, genes that confer insect resistance, genes that confer disease resistance, genes that confer drought resistance, genes that improve nutritional value, genes that improve yield or quality, and genes that affect plant fertility) as well as transcription regulation sequences (e.g., a promoter and transcription terminator) to control expression of the trait gene. These regulatory sequences include, but are not limited to, constitutive plant promoters such as the NOS promoter, The 35S promoter, or the UBI promoter, chemically-inducible gene promoters such as the dexamethasone-inducible promoter (see, e.g., Gremillon et al. (2004), *Plant J.* 37:218-228), and plant tissue specific promoters such as the LGC1 promoter (see, e.g., Singh et al. (2003), FEBS Lett. 542:47-52).

As used herein, the term "homologous recombination" refers to a natural, cellular process in which a double-stranded DNA-break is repaired using a homologous DNA sequence as the repair template (see, e.g., Cahill et al. (2006), *Front. Biosci.* 11:1958-1976). Thus, in some embodiments, the LIG-34 meganuclease is used to cleave the LIG-34 recognition site in a maize cell and a sequence of interest flanked by DNA sequence with homology to the LIG-34 recognition site is delivered into a maize cell and used as a template for repair by homologous recombination. The sequence of interest is thereby incorporated into LIG-34 recognition site.

As used herein, the term "non-homologous end-joining" refers to a natural, cellular process in which a double-stranded DNA-break is repaired by the direct joining of two non-homologous DNA segments (see, e.g., Cahill et al. (2006), *Front. Biosci.* 11:1958-1976). DNA repair by non-homologous end joining is error-prone and frequently results in the capture of exogenous DNA sequences at the site of repair joining (see, e.g., Salomon, et al. (1998), *EMBO J.* 17:6086-6095). This is particularly true of exogenous DNA sequences delivered by *Agrobacterium tumefaciens*. Thus, in certain embodiments, the LIG-34 meganuclease can be used to produce a double-stranded break at the LIG-34 recognition site in a maize cell and a sequence of interest, which may or may not have homology to the LIG-34 recognition site, can be delivered to a maize cell and be captured at the LIG-34 site by non-homologous end joining. The sequence of interest is, thereby, incorporated into the LIG-34 recognition site.

As a general matter, methods for delivering nucleic acids to maize cells are well known in the art and include *Agrobacterium* infection, PEG-mediated transformation of protoplasts (Omirulleh et al. (1993), *Plant Molecular Biology*, 21:415-428), desiccation/inhibition-mediated DNA uptake, electroporation, agitation with silicon carbide fibers, ballistic injection or microprojectile bombardment, biolistic injection (Lorence and Verpoorte (2004), *Methods Mol. Biol.*, 267: 329-50) and the like. Also, as a general rule, the method of gene delivery can be correlated with the activity level of the LIG-34 meganuclease. Meganucleases with lower activity (e.g., SEQ ID NO: 1) are advantageously delivered by *Agrobacterium* infection or a related method which efficiently produces stable transformants (i.e. produces plants in which the LIG-34 gene is integrated stably into the plant genome). This is because long-term exposure to meganuclease is more likely to yield high-efficiency DNA cleavage by such reduced-activity meganucleases. On the other hand, microprojectile bombardment of plasmid DNA, biolistic injection, or similar methods which can result in transient gene delivery (i.e. the meganuclease gene is NOT integrated into the genome and is NOT selected for and, thus, is lost over time) are advantageous for delivering very high activity LIG-34 meganucleases (such as SEQ ID NO: 13) because long-term exposure to a high-activity LIG-34 meganuclease is not necessary for high-efficiency cleavage of the LIG-34 recognition sequence and may lead to toxicity due to off-target DNA cleavage.

In some embodiments, the methods of the invention involve the delivery of a sequence of interest as well as the gene encoding the LIG-34 meganuclease into a single maize cell or embryo which can be grown into a mature recombinant maize plant and give rise to progeny carrying the inserted sequence of interest in its genome.

3.1 Methods for Inserting a Sequence of Interest into the LIG-34 Recognition Site by Homologous Recombination Aspects of the invention allow for the use of the LIG-34 meganuclease to introduce a sequence of interest into the LIG-34 recognition site by homologous recombination. Such methods require two components:

1. The LIG-34 expression cassette. This component is a DNA molecule encoding the LIG-34 meganuclease under the control of a promoter suitable for the expression of the meganuclease gene in a maize cell. Such promoters are known in the art and include, preferably, constitutive plant promoters such as the nopaline synthase (nos) promoter, the CaMV 35S promoter, or the plant ubiquitin (Ubi) promoter. In addition, for some embodiments, chemically-inducible gene promoters such as the dexamethasone-inducible promoter (see, e.g., Gremillon et al. (2004), *Plant J.* 37:218-228), and plant tissue specific promoters such as the LGC1 promoter (see, e.g., Singh et al. (2003), FEBS Lett. 542:47-52) may be used. In general, the choice of promoter may be correlated with the activity level of the LIG-34 meganuclease and/or choice of gene delivery method. For example, strong, constitutive promoters such as Ubi or CaMV 35S are preferred for low-activity LIG-34 meganucleases (such as SEQ ID NO: 1) and for applications in which the meganuclease gene is delivered transiently (such as microprojectile bombardment in the absence of selection for stable transformants). On the other hand, inducible promoters, tissue-specific promoters, or weak constitutive promoters are preferred for high-activity meganucleases (such as SEQ ID NO: 13) in cases where the meganuclease expression cassette is stably integrated into the plant genome for long-term expression of the meganuclease gene. Preferably, the LIG-34 meganuclease coding sequence will be optimized for expression in eukaryotic cells (e.g., SEQ ID NO: 9). Also preferably, the LIG-34 gene will be followed by a transcription terminator sequence such as the nopaline synthase (nos) terminator.

2. The homologous donor cassette. This component is a DNA molecule harboring a sequence of interest flanked on one or, preferably, both sides by regions of homology to the LIG-34 recognition site. The region(s) of homology will be at least 50 base pairs in length and can be, 50-900, 50-1000, 500-900, or 500-1000 base pairs in length. In preferable embodiments, the sequence of interest will be flanked on one side by 50-900, 50-1000, 500-900, or 500-1000 bases that are identical or nearly identical to the DNA sequence immediately 5' of the LIG-34 recognition sequence (including the 5' LIG-34 recognition half-site) and will be flanked on the other side by 50-900, 50-1000, 500-900, or 500-1000 bases that are identical or nearly identical to the DNA sequence immediately 3' of the LIG-34 recognition sequence (including the 3' LIG-34 recognition half-site). For example, an effective donor cassette may have the following composition: 5'-[50-900 consecutive base pairs SEQ ID NO: 10]-[sequence of interest]-[50-900 consecutive base pairs SEQ ID NO: 11]-3'. In another example, an effective donor cassette may have the following composition: 5'-[50-1000 consecutive base pairs SEQ ID NO: 10]-[sequence of interest]-[50-1000 consecutive base pairs SEQ ID NO: 11]-3'. The homologous donor cassette may or may not be harbored on the same DNA molecule as the LIG-34 expression cassette.

In preferred embodiments, the LIG-34 expression cassette and the homologous donor cassette are delivered simultaneously to individual maize cells or maize embryos. In other embodiments, the LIG-34 expression cassette is delivered first to individual maize cells or maize embryos and the homologous donor cassette is delivered subsequently to the same cell or embryo. Transformed cells are then grown into calli or plants and are screened (e.g., by PCR) for individuals in which the sequence of interest integrated into the LIG-34 recognition site by homologous recombination or non-homologous end joining. In certain embodiments, the sequence of interest is a selectable marker gene (e.g., an herbicide resistance gene) and transformed plants can be selected for under the appropriate growth conditions (e.g., in the presence of herbicide) followed by molecular screening to identify individuals in which the sequence of interest integrated at the LIG-34 recognition site.

3.2 Methods for Inserting a Sequence of Interest into the LIG-34 Recognition Site by Non-Homologous End-Joining Aspects of the invention allow for the use of the LIG-34 meganuclease to introduce a sequence of interest into the LIG-34 recognition site by Non-Homologous End-Joining Such methods require two components:

1. The LIG-34 expression cassette. This component is as described in 3.1 above.

2. The non-homologous donor cassette. This component comprises, at a minimum, the sequence of interest with no additional DNA sequence. In some embodiments, the non-homologous donor cassette may comprise the sequence of interest flanked on one or both sides by the LIG-34 recognition sequence. In the latter case, cleavage of the non-homologous donor cassette by the LIG-34 meganuclease will result in four basepair 3' "sticky ends" on one or both sides of the sequence of interest that are compatible with the sticky ends produced by cleavage of the LIG-34 recognition site which may facilitate integration of the sequence of interest by non-homologous end joining. The non-homologous donor cassette may be housed on the same DNA molecule as the LIG-34 expression cassette only if the two are separated by a LIG-34 recognition sequence which can be cut by the LIG-34 meganuclease inside of the cell to separate the two cassettes from one another.

In preferred embodiments, the LIG-34 expression cassette and the non-homologous donor cassette are delivered simultaneously to individual maize cells or maize embryos. In other embodiments, the LIG-34 expression cassette is delivered first to individual maize cells or maize embryos and the homologous donor cassette is delivered subsequently to the same cell or embryo. Transformed cells are then grown into calli or plants and are screened (e.g., by PCR) for individuals in which the sequence of interest integrated into the LIG-34 recognition site by non-homologous end joining. In certain embodiments, the sequence of interest is a selectable marker gene (e.g., an herbicide resistance gene) and transformed plants can be selected for under the appropriate growth conditions (e.g., in the presence of herbicide) followed by molecular screening to identify individuals in which the sequence of interest integrated at the LIG-34 recognition site.

3.3 Methods for Inserting a Sequence of Interest into the LIG-34 Recognition Site by Homologous Recombination In a Maize Plant PCT application WO/2009/006297 describes in vivo activity and uses of the LIG-34 meganuclease in a maize plant (see FIG. 10 and Example 6, pgs. 70-77 of WO/2009/006297, which are incorporated by reference herein). This demonstrates the in vivo activity of LIG34 meganucleases and their usefulness for genetic engineering of plants such as maize.

EXAMPLES

Example 1

In Vitro DNA Cleavage Activity of the LIG-34 Meganucleases

1. Expression and Purification of LIG-34 meganucleases

Genes encoding LIG-34, LIG-34+, and LIG-34++ (SEQ ID NO: 1, SEQ ID NO: 12, and SEQ ID NO: 13) were assembled by PCR and cloned into a bacterial expression vector (pET-21a, Novagen Corp., San Diego, Calif.) with a C-terminal 6x-his tag (SEQ ID NO: 14) to facilitate purification. The plasmids were then used to transform chemically competent BL21 (DE3) pLysS E. coli, which were plated on standard 2xYT plates containing 200 μg/ml carbanicillin. Following overnight growth, transformed bacterial colonies were scraped from the plates and used to inoculate 50 ml of 2XYT broth. Cells were grown at 37° C. with shaking until they reached an optical density of 0.6-0.8 at a wavelength of 600 nm. The growth temperature was then reduced from 37° C. to 25° C. Protein expression was induced by the addition of 1 mM IPTG, and the cells were incubated with agitation for three hours. Cells were then pelleted by centrifugation for 10 min. at 6000×g. Pellets were resuspended in 1 ml binding buffer (20 mM Tris-HCL, pH 8.0, 500 mM NaCl, 10 mM imidazole) by vortexing. The cells were then disrupted with 12 pulses of sonication at 50% power and the cell debris was pelleted by centrifugation for 15 min. at 14,000×g. Cell supernatants were diluted in 4 ml binding buffer and loaded onto a 200 μl nickel-charged metal-chelating Sepharose column (Pharmacia).

The column was subsequently washed with 4 ml wash buffer (20 mM Tris-HCl, pH 8.0, 500 mM NaCl, 60 mM imidazole) and with 0.2 ml elution buffer (20 mM Tris-HCl, pH 8.0, 500 mM NaCl, 400 mM imidazole). Meganuclease enzymes were eluted with an additional 0.6 ml of elution buffer and concentrated to 50-130 μl using Vivospin disposable concentrators (ISC, Inc., Kaysville, Utah). The enzymes were exchanged into SA buffer (25 mM Tris-HCL, pH 8.0, 100 mM NaCl, 5 mM MgCl$_2$, 5 mM EDTA) for assays and storage using Zeba spin desalting columns (Pierce Biotechnology, Inc., Rockford, Ill.). The enzyme concentration was determined by absorbance at 280 nm using an extinction coefficient of 47180 M$^{-1}$cm$^{-1}$. Purity and molecular weight of the enzymes was then confirmed by gel electrophoresis and/or MALDI-TOF mass spectrometry.

2. Cleavage Assays

The LIG-34 meganucleases were assayed for in vitro activity by incubation with linear, double-stranded DNA substrates containing the meganuclease recognition sequence. Synthetic oligonucleotides corresponding to both sense and antisense strands of the LIG-34 recognition site (SEQ ID NO: 2, SEQ ID NO: 3) were annealed and cloned into the SmaI site of the pUC19 plasmid by blunt-end ligation. The plasmid substrate was linearized with XmnI concurrently with the meganuclease digest. The enzyme digests contained 5 μl of 0.05 μM DNA substrate, 5 μl of meganuclease at varying concentrations (diluted in SA buffer, see below), 14.5 μl SA buffer, and 0.5 μl XmnI. LIG-34 enzyme concentration was varied from 5-400 nM (final concentration). Digests were incubated at 37° C. for 1 hour. Digests were stopped by adding 0.3 mg/ml Proteinase K and 0.5% SDS, and incubated for one hour at 37° C. Digests were analyzed on 1.5% agarose and visualized by ethidium bromide staining.

Digestion of the linearized plasmid with LIG34, LIG34+ or LIG34++ meganuclease produced two bands on the gel of the sizes corresponding to a simple cut at the LIG-34 site. All of the LIG-34 meganucleases efficiently cut the plasmid substrate harboring the LIG-34 recognition site. $C_{50}$ values (the concentration of meganuclease required to cut 50% of the 10 nM plasmid substrate to completion in 1 hour) were found to be ~16 nM, ~13 nM, and ~11 nM for, respectively, LIG-34, LIG-34+, and LIG-34++. Thus, while all three enzymes efficiently cleave the LIG-34 site sequence, they do so with varying activity levels (LIG-34<LIG-34+<LIG-34++).

Example 2

In Vivo DNA Cleavage Activity of the LIG-34 Meganucleases

1. DNA Break/Repair Assay in a Human Cell Line

LIG-34, LIG-34+, and LIG-34++ were evaluated for DNA cleavage activity in a reporter assay in a human cell-line as follows: a defective GFP reporter cassette was generated by first cloning a 5' 480 bp fragment of the GFP gene into NheI/HindIII-digested pcDNA5/FRT (Invitrogen Corp., Carlsbad, Calif., USA) resulting in the plasmid, pGF. Next, a 3' 480 fragment of the GFP gene (including a 240 bp sequence duplicated in the 5' 480 bp fragment) was cloned into BamHI/XhoI-digested pGF. The resulting plasmid, pGFFP, consists of the 5' ⅔rd of the GFP gene followed by the 3' ⅔rd of the GFP gene, interrupted by 24 bp of the pcDNA5/FRT polylinker. To insert the LIG-34 recognition site into pGFFP, complimentary oligonucleotides encoding the binding site were annealed and ligated into HindIII/BamHI-digested pGFFP, resulting in pGFFP.LIG34. This plasmid comprises, in 5' to 3' orientation: a CMV promoter, the 5' ⅔ of the GFP gene, a LIG-34 recognition site sequence, the 3' ⅔ of the GFP gene, and a BGH polyadenylation signal. In vivo cleavage of the LIG-34 site by the LIG-34 meganuclease is expected to stimulate homologous recombination between the two direct repeats of the GFP gene to yield a functional GFP gene (FIG. 2). 293.GFFP.LIG34 cells were generated by stably integrating this reporter cassette into the genome of Flp-In 293 cells using the Flp-In system according to the manufacturer's instructions (Invitrogen Corp., Carlsbad, Calif., USA).

The coding sequences of LIG-34, LIG-34+, and LIG-34++ were inserted into to the mammalian expression vector pCI (Promega) under the control of a constitutive (CMV) promoter. 293.GFFP.LIG34 cells at ~90% confluence were transfected in 24-well plates with either 800 ng pCI GFP (to determine transfection efficiency), 800 ng empty pCI (no enzyme control) or 400 ng pCI encoding LIG-34, LIG-34+, or LIG-34++ balanced with 400 ng empty pCI, using Lipofectamine 2000 according to the manufacturer's instructions (Invitrogen Corp., Carlsbad, Calif., USA). 96 hours post-transfection, cells were washed in PBS, trypsinized, and resuspended in PBS supplemented with 3% FBS. Cells were assayed for GFP activity using a Cell Lab Quanta SC MPL flow cytometer and the accompanying Cell Lab Quanta Analysis software (Beckman Coulter).

It was found that 293.GFFP.LIG34 cells were GFP+ with frequencies of 2.5%, 5.3%, and 7.1%, respectively, when expressing LIG-34, LIG-34+, and LIG-34++ (FIG. 3). Cells transfected with an empty pCI expression vector were <°0.1% GFP+. These results indicate that the LIG-34 meganucleases are capable of cleaving the LIG-34 recognition site in vivo with the expected order of activities.

What is claimed is:

1. A rationally-designed meganuclease having the amino acid sequence of SEQ ID NO: 1.

2. A rationally-designed meganuclease having the amino acid sequence of SEQ ID NO: 12.

3. A rationally-designed meganuclease having the amino acid sequence of SEQ ID NO: 13.

* * * * *